United States Patent
Fehr et al.

(10) Patent No.: US 6,262,288 B1
(45) Date of Patent: Jul. 17, 2001

(54) PROCESS FOR THE PREPARATION OF CHIRAL EPOXIDES

(75) Inventors: Charles Fehr, Versoix (CH); Eric Ohleyer, Cruseilles (FR); José Galindo, Les Avanchets (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/553,547

(22) Filed: Apr. 20, 2000

Related U.S. Application Data

(63) Continuation of application No. PCT/IB99/00760, filed on Apr. 27, 1999.

(51) Int. Cl.[7] .................................................. C07F 7/00
(52) U.S. Cl. ........................... 556/440; 556/437; 549/512
(58) Field of Search ..................................... 556/440, 437; 549/512

(56) References Cited

U.S. PATENT DOCUMENTS

| 4,882,451 | * | 11/1989 | Yoshida et al. |
| 5,714,351 | * | 2/1998 | Evans et al. |
| 5,962,706 | * | 10/1999 | Fehr . |

FOREIGN PATENT DOCUMENTS

841331 * 5/1998 (EP) .

OTHER PUBLICATIONS

Fehr et al. "A new variant of the Claisen rearrangement from malonate–derived allylic trimethylsiyl ketene acetals:—", Angew. Chem., Int. Ed. (2000) 39(3), 569–573.*

* cited by examiner

Primary Examiner—Ralph Gitomer
Assistant Examiner—D. Khare

(74) Attorney, Agent, or Firm—Winston & Strawn

(57) ABSTRACT

The invention describes novel malonates and a process for using said malonates for the preparation of chiral epoxides of formula

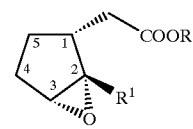
(I)

having a cyclanic (1R) configuration, the group in position 2 having a transconfiguration and the epoxy group having a cis-configuration with respect to the substituent in position 1 and wherein R is an alkyl group from $C_1$ to $C_4$, linear or branched, and $R^1$ is an alkyl or an alkenyl group from $C_2$ to $C_8$, linear or branched. The above process comprises the rearrangement of malonate (VII) to malonate (VI) and the decarboxylation reaction of

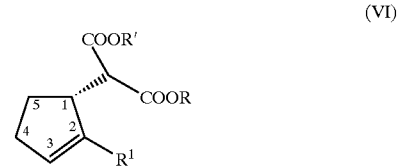
(VI)

into an ester of formula

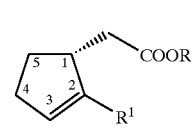
(III)

followed by the stereoselective epoxidation of the thus-obtained compound.

7 Claims, No Drawings

PROCESS FOR THE PREPARATION OF CHIRAL EPOXIDES

This appln is a continuation of PCT/IB99/00760 filed Apr. 27, 1999.

BRIEF SUMMARY OF THE INVENTION

The present invention relates to the field of organic synthesis. It relates, more particularly, to novel malonates cited below and their use in the novel synthesis of chiral epoxides of formula

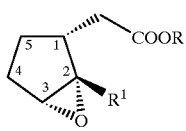
(I)

having a cyclanic (1R) configuration, the group in position 2 of the ring having a transconfiguration and the epoxy group having a cis-configuration with respect to the substituent in position 1 of the ring. In the above formula (I), R is a linear or branched alkyl group from $C_1$ to $C_4$ and $R^1$ is a linear or branched alkyl, alkylene or alkynyl group from $C_4$ to $C_6$. The present invention is in particular drawn towards the synthesis of epoxides according to the above formula (I) in which R is a methyl group and $R^1$ is a (Z)-2-pentenyl group.

BACKGROUND OF THE INVENTION

The epoxides of the above formula (I) are of great interest in the fragrance industry as precursors for the synthesis of ketones of the formula (II), into which they are transformed in a rearrangement reaction which, depending on the conditions chosen, may proceed in a stereochemically selective way.

(I) →  (II)

The ketones of formula (II), which show a (1R)-cis configuration, form a class of fragrant molecules developing a jasmine-like odour which varies depending on the nature of the substituents R and $R^1$. It has been found that the molecules possessing the configuration (1R)-cis, as shown in the above formula (II), are exactly those responsible for the typical jasmine odour of the compounds, whereas the other 3 stereoisomers contribute to a much lesser extent to the mentioned, and highly appreciated jasmine odour.

Of particular interest for perfumers are the two molecules of formula (II) in which R is a methyl group and $R^1$ is either a n-pentyl or a (Z)-2-pentenyl group. These compounds represent best the jasmine odour which is so prized by perfumers. In what concerns the compound in which $R^1$ is a n-pentyl group, this compound has been synthetically available for some time now, for example by enantioselective hydrogenation of appropriate precursor compounds (see U.S. Pat. No. 5,874,600 and WO 98/52687, both to Firmenich S A). Another synthesis for this compound and for its (Z)-2-pentenyl analogue, which is related to the present invention, is described in U.S. Pat. No. 5,962,706 (applicant: Firmenich S A), which will be discussed in greater detail below.

A process for the synthesis of the epoxides of the above-mentioned formula (I) is described in U.S. Pat. No. 5,962,706 (applicant: Firmenich S A). This synthesis comprises the reaction steps which are outlined in the following scheme I.

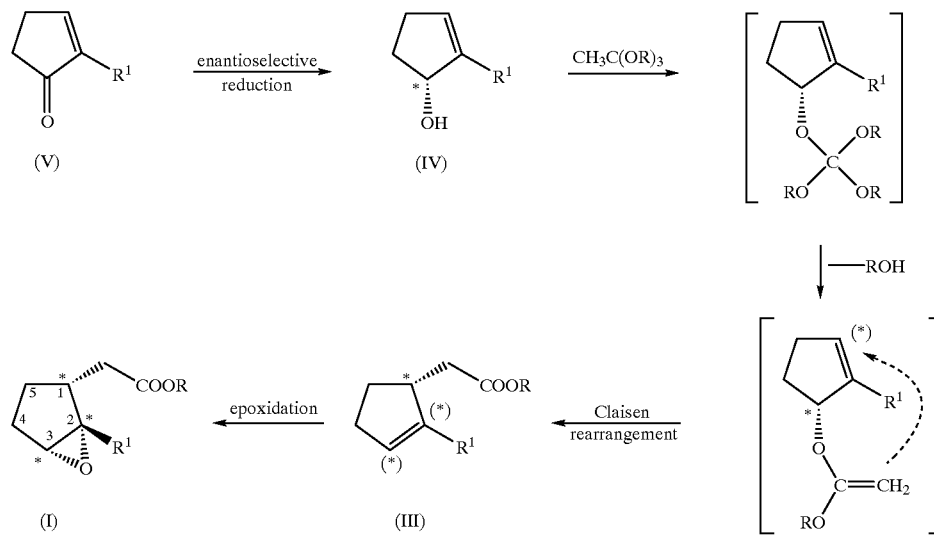

Scheme I

The above synthesis, although giving high enantiomeric excesses (ee's), of the order of greater than 95%, and high yields and allowing thus to prepare the desired epoxides (I) having the defined stereochemistry, can still be improved in order to raise the overall yield and reduce the costs of the synthesis. In particular, the synthesis of the ester (III), starting from the chiral alcohol (IV), is hampered by the fact that the intermediate products (designed in brackets) which are obtained after the esterification reaction with an orthoester $CH_3C(OR)_3$ have to be treated at a relatively high temperature of above 140° C. in order to induce the Claisen rearrangement reaction which gives the desired ester (III), from which are prepared the epoxides (I). Therefore, in the case where the esterification of the alcohol (IV) is carried out with trimethylorthoacetate ($R=CH_3$), an incomplete rearrangement reaction results because the intermediate ester can only be heated to about 115° C., due to its low boiling point. Thus, use of triethylorthoacetate ($R=C_2H_5$), or even higher analogues is required, in which case the intermediate esters show higher boiling points, permitting a complete conversion in the Claisen rearrangement reaction leading towards the ester (III). However, because the most appreciated compounds of formula (II) are the methyl esters ($R=CH_3$), a supplementary transesterification or saponification/esterification reaction has to be carried out after the rearrangement reaction has taken place, thus raising costs and lowering yields.

DESCRIPTION OF THE INVENTION

The object of the present invention is to provide a process for the preparation of esters of the above formula (III) which improves on the process described in U.S. Pat. No. 5,962,706.

This object is attained by a process for the preparation of an ester of formula

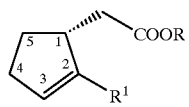

(III)

having a (1R) configuration, and wherein R is an alkyl group from $C_1$ to $C_4$, linear or branched, and $R^1$ is an alkyl, alkenyl or alkynyl group from $C_4$ to $C_6$, linear or branched, which process comprises the decarboxylation reaction of a compound of formula

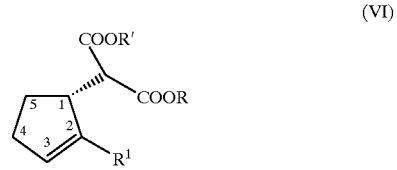

(VI)

wherein R and $R^1$ have the meaning given above and R' is hydrogen or a triorganylsilyl group.

In a preferred embodiment of the invention, R is a methyl group, R' is a trimethylsilyl group, and $R^1$ is a pentyl or a (Z)-2-pentenyl group.

The compounds (VI) are novel chemical species which are the object of the invention and turn out to be unexpectedly advantageous for the preparation of the desired fragrance ingredients of formula (II) and the intermediates therefor.

The use of these novel compounds (VI) according to the present invention renders it possible to prepare esters (III), and ultimately the epoxides (I), in a simple and very efficient one-pot reaction.

The novel compounds (VI) are used in a decarboxylation reaction leading to the esters (III), which reaction is carried out for example by saponification of one ester function, which saponification may be carried out under basic and acidic conditions. In the case where R' is an organosilyl group, e.g. a trimethylsilyl group, it was found to be particularly advantageous when N-methylpyrrolidone (NMP) and water were used for the hydrolysis reaction.

Furthermore, we were able to develop original processes for the preparation of malonates (VI). One synthetic route is outlined in the following scheme II, in which R, R' and $R^1$ have the meaning given above.

Scheme II

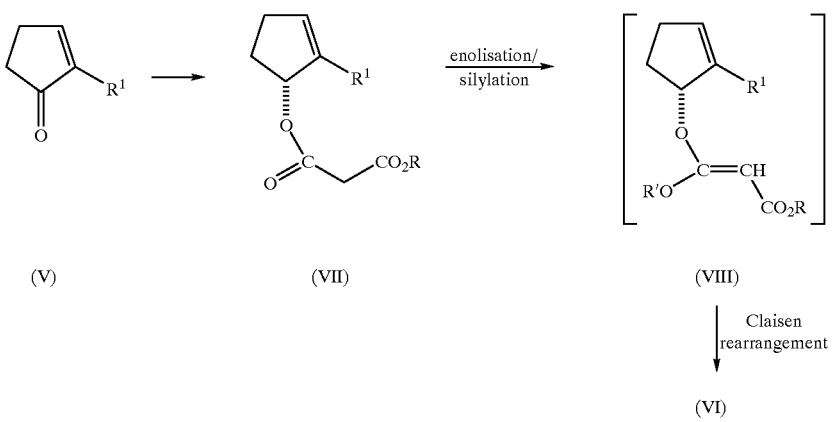

This synthesis starts from the known cyclopentenones (V). The ketone is converted into the novel chiral, mixed malonic ester (VII) having the configuration (1R). This transformation may be carried out in different ways.

According to the invention the ketone is reduced in an enantioselective manner, into the corresponding cyclopentenol having a (1R) cyclanic configuration, and the latter is then esterified with an appropriate derivative of malonic acid, e.g. an ester thereof, the esterification being carried out under conditions which allow the retention of the stereochemistry of the chiral carbon. Specific conditions are described in detail in the examples.

The enantioselective reduction of the keto function is carried out using techniques which are known in the art. Advantageous results could be obtained when using a reductive system of the oxazaborolidine-borane type (see, for example, E. J. Corey et al., J. Amer. Chem. Soc. 1987, 109, 7925; S. Itsuno et al., Bull. Chem. Soc. Jpn. 1987, 60, 395; D. J. Mathre et al., J. Org. Chem. 1991, 56, 751; V. K. Singh, Synthesis 1992, 605).

The cyclopentenones of formula (V) can also be reduced into the desired racemic alcohols by a conventional transformation, followed by esterification into the racemic ester such as, for example, the acetate. The racemic esters are then separated in a biotechnological process which involves the enantioselective saponification into the desired optically active alcohols by means of a lipase. Examples of suitable lipases include *Candida antarctica, Pseudomonas fluorescens, Pseudomonas cepacia, Mucor miehei, Chromabacterium viscosum* and *Mucor javanicus*.

The chiral cyclopentenol having the (1R)-configuration is then esterified without racemization into the malonic diester (VII). This esterification is carried out, for example, by using an alkyl malonyl halide such as, for example, methyl malonyl chloride. The use of this reagent is preferred according to the invention, resulting in mixed malonates (VII) in which R is a methyl group.

Another synthetic route to obtain the novel chiral malonates (VII) is the conventional reduction of the cyclopentenone (V) into the corresponding racemic alcohols, followed by an enantiodiscriminating esterification or transesterification into the said chiral malonates. This original synthetic route is preferred according to the present invention. Of course, this enzymatic esterification can also be performed on a non-racemic (1R)-(IV) alcohol.

The said racemic reduction can be carried out by using a convenient reducing agent such as $LiAlH_4$. The enantioselective esterification or transesterification according to the invention of the thus-obtained racemic cyclopentenols involves the use of a lipase, together with an appropriate derivative of malonic acid. Non limiting examples for the named derivatives include monoesters of malonic acid and diesters of malonic acid, which latter may be mixed esters (of two different alcohols) and non-mixed ester (of one alcohol). In the context of the present invention, it is preferred to use a derivative of malonic acid in which at least one carboxylic group is esterified by methanol. The most preferred derivative of malonic acid is dimethylmalonate.

The lipases which are appropriate for use in the esterification or transesterification reaction according to the present invention are commercial enzymes and include, for example, *Candica antarctica, Pseudomonas fluorescens, Pseudomonas cepacia, Candida cylindracea, Mucor miehei, Chromabacterium viscosum* and *Rhisopus arrhizus*. Preferred lipases according to the invention are selected from *Candida antarctica* [namely Novozyme® 435 (Novo Nordisk) and Chyrazyme® L-2 or C-2 (Roche)], *Mucor miehei* (namely Lypozyme® IM; origin: Novo Nordisk) and Alcaligenes spp. (namely Lipase QLM; origin: Meito Sangyo; Chyrazyme® L 10; origin: Roche). The enzymes can be used in immobilized form.

The most advantageous results regarding the preparation of the malonic ester (VII) could be obtained when the racemic cyclopentenol (obtained from the starting ketone (V) in a non-enantioselective reduction) was reacted with dimethylmalonate in the presence of catalytic amounts of a lipase, preferably *Candida antarctica* or Alcaligenes spp. In this way, enantiomeric excesses (ee's) greater than 97% could be obtained.

In the next reaction step, the mixed malonate (VII) is enolized and converted into the unstable ketene acetal (VIII), which undergoes a smooth Claisen rearrangement, resulting in the desired malonate (VI). The enolization of the mixed malonate (VII), i.e. the abstraction of the proton in a-position to the carbonyl groups, is attained by means of reagents such as, for example, hydrides or other bases. More specific examples for these reagents include alcoholates, amides and alkaline and alkaline earth alkaline hydrides. Preferred proton abstracting agents are NaH, KH and hexamethyldisilazane sodium salt.

Subsequent reaction of the resulting enolate with an appropriate electrophile R'X results in the ketene acetal (VIII). The groups which are appropriate for a use in the present invention include organosilane groups, the most preferred group being the trimethylsilane group. The introduction of this group facilitates the rearrangement reaction and it is easy to saponify, facilitating also the decarboxylation. The trimethylsilyl derivative is obtainable by the reaction of the enolate with trimethylchlorosilane.

Alternatively, it is also possible to treat the enolate with a Lewis-acidic metal salt such as, for example, $ZnCl_2$ (R'=ZnCl).

The resulting ketene acetal (VIII) undergoes a Claisen-rearrangement reaction under smooth conditions, it being unnecessary to heat the acetal to temperatures close to 150° C. The rearrangement reaction proceeds stereospecifically, resulting in the substituted malonate of formula (VI), which can then be used to prepare the ester of formula (III), both having a cyclanic (1R)-configuration, in enantiomeric excesses of up to greater than 97%.

The cyclopentenyl esters (III) which can be obtained by using malonate (VI) according to the processes described above can be epoxidized to the chiral epoxides (I) in a specific epoxidation process which makes use of strong organic peracids, in general peracids which carry strongly electron-withdrawing groups. In this context, permaleic acid, perphthalic acid, m-chloroperbenzoic acid or perhalogenated acids of formula $CX_3COO_2H$, wherein X stands for a halogen atom, in particular chlorine or fluorine, can be cited as preferred agents. The most preferred peracids are permaleic and trifluoroperacetic acid. The epoxidizing agents will preferably be used in a chlorinated solvent, the most preferred being dichloromethane.

The use of the above-specified specific agents allows the selective epoxidation of the esters (III) in cis-position to the —$CH_2COOR$-group in position 1 of the cycle. This selectivity is necessary in order to obtain the fragrant ketones (II) in a diastereoselective way. Furthermore, in the case where the substituent $R^1$ is a (Z)-2-pentenyl group, we were surprised to find that the use of the above-specified epoxidation agents also made it possible to epoxidize the double bond in the cyclopentenyl ring in a practically selective way, with the double bond in the side chain remaining unaffected.

In summary, the present invention provides novel malonates (VI) and the easy preparation thereof, which malonates are useful for the preparation of fragrant ketones having a defined stereochemistry.

The invention will now be described in greater detail in the following examples in which the temperatures are indicated in degrees centigrade, the data of the NMR-spectra indicate the chemical shift δ in ppm with respect to TMS as internal standard, and the abbreviations have the usual meaning in the art.

PREFERRED EMBODIMENTS OF THE INVENTION

EXAMPLE 1

Preparation of (+)-methyl (R)-2-pentyl-2-cyclopenten-1-yl malonate

A mixture of racemic 2-pentyl-2-cyclopenten-1-ol (55.0 g; 357 mmol), dimethyl malonate (55.0 g; 417 mmol) ground $KHCO_3$ (1.78 g; 17.8 mmol) and Novozym 435® (immobilized *Candida antarctica* from Novo Nordisk; 5.50 g) was gently swirled in a 250 ml flask connected to a Büchi rotavapor at 40° C. and 53 hPa. After 60 min., the product was filtered, washed (sat. aq. $NaHCO_3$, sat. aq. NaCl), dried ($Na_2SO_4$) and concentrated (112.4 g). Distillation at 110° C./1 hPa afforded 32.26 g (71%) of (+)-methyl-(R)-2-pentyl-2-cyclopenten-1-yl malonate in 97% ee.

$[\alpha]^{20}_D$=+8.7 ($CHCl_3$)

$^1$H-NMR: 0.89(t, J=7, 3H); 1.29(m, 4H); 1.46(m, 2H); 1.81(m, 1H); 2.04(m, 2H) 2.20–2.50(m, 3H); 3.38(s, 2H); 3.74(s, 3H); 5.69(broad s, 1H); 5.72(m, 1H).

$^{13}$C-NMR: 167.1(s); 166.3(s); 142.3(s); 130.3(d); 82.8(d); 52.4(q); 41.7(t); 31.7(t); 30.8(t); 30.2(t); 28.1(t); 27.2(t); 22.5(t); 14.1(q).

MS (electron spray): 276.8 $[M+Na]^+$, corresponds to a molecular weight of 253.8.

EXAMPLE 2

Preparation of (+)-methyl (1R)-2-pentyl-2-cyclopentene-1-acetate

The compound obtained in Example 1 (25.10 g; 98.8 mmol) was added at 60° C. within 35 min. to a mechanically stirred suspension of unwashed NaH [55% in oil; 5.17 g (=2.84 g pure NaH); 118 mmol] in THF (210 ml) (350 ml 3-necked flask, $N_2$). Immediate gas-evolution ($H_2$) was observed, as well as the formation of a new precipitate. After 1 h, trimethylchlorosilane (16.09 g, 148.2 mmol) was added in 20 min. After refluxing the milky reaction mixture for 3 h, the reaction did not progress any more. The reaction mixture was concentrated at 60° C./8 hPa, treated with N-methyl-pyrrolidone (145.3 g) and heated under distillative conditions, until the temperature stabilized at ca. 135° C. At this point, 3 ml of water were added (temp. 120° C.) and heating continued with concomitant distillative removal of residual THF, water and a silane. Another portion of water (3.02 g, 168 mmol) was added to the hot mixture (148° C.) and heating continued under non-distillative conditions (140-145° C.). The gas-evolution ($CO_2$) ceased after 15 min., indicating the end of the reaction. The cooled reaction mixture was poured into water, and the desired ester was extracted with ether and washed with $H_2O$, then again washed with 5% sat. aq. NaOH, $H_2O$, sat. aq. NaCl, dried ($Na_2SO_4$), filtered and concentrated. Bulb-to-bulb distillation of the residue (24.5 g) at 100–120° C. (oven temp.)/0.05 hPa afforded a main fraction of the desired methyl ester (16.90 g, 86% pure, 70% yield; 97% ee). The head- and tail fractions were discarded.

$[\alpha]^{20}_D$=+25.3 (c=3.6; $CHCl_3$)

NMR($^1$H, 360 MHz): 0.89(t, J=7, 3H); 1.20–1.60(m, 7H); 1.85–2.35(m, 6H); 2.54(dd, J=15 and 4, 1H); 2.93(broad, 1H); 3.67(s, 3H); 5.37(broad s, 1H) δ ppm.

NMR($^{13}$C): 14.1(q); 22.6(t); 27.4(t); 28.9(t); 30.4(t); 30.5(t); 31.8(t); 38.5(t); 43.6(d); 51.5(q); 124.4(d); 146.2(s); 173.8(s) δ ppm.

MS: 210($M^+$, 32), 178(3), 150(16), 136(59), 121(13), 107(23), 93(43), 80(100), 67(42), 41(36), 29(31).

The analogous product with a n-hexyl side chain, i.e. (+)-methyl-(1R)-2-hexyl-2-cyclopentene-1-acetate, is obtained in the same reaction sequence as described in Examples 1 and 2, replacing the 2-pentyl-2-cyclopentenol by 2-hexyl-2-cyclopentenol. The final product (+)-methyl-(1R)-2-hexyl-2-cyclopentene-1-acetate was obtained in 95% ee. The desired product showed a retention time of 21.41 min (21.63 for its enantiomer of configuration (IS), measured on a column of the type Megadex 5 using a temperature program starting at 90° C. (constant for 6 min), then heating to 180° C. at a rate of 2.5° C./min and a hydrogen pressure of 16.9 psi). The analytical data were the following:

NMR($^1$H): 0.88(distorted t, J=7, 3H); 1.28(broad, 7H); 1.30–1.60 (m, 2H); 1.85–2.35(m, 6H); 2.54 (dd, J=15 and 4, 1H); 2.94(m, 1H); 3.67(s, 3H); 5.36 (broad split s, 1H) δ ppm.

NMR($^{13}$C): 173.8(s); 146.2(s); 124.3(d); 51.5(q); 43,6(d); 38.5(t); 31.8(t); 30.5(t); 30.4(t); 29.3(t); 29.0(t); 27.6(t); 22.7(t); 14.1(q) δ ppm.

MS: 224($M^+$, 17), 164(15), 150(50), 121(20), 107(21), 93(51), 80(100), 67(47), 41(62).

EXAMPLE 3

Preparation of methyl trimethylsilyl (1R)-2-(2-pentyl-2-cyclopenten-1-yl)malonate The title product, i.e. the intermediate silylated malonic ester obtained after the Claisen-rearrangement and corresponding to the compound of formula (VI), can also be isolated. To this end, the reaction as described in Example 2 was interrupted after the addition of trimethylchlorosilane and refluxing the mixture for 3 hours. The mixture was then concentrated at 25° C. under reduced pressure, treated with pentane and filtered through silica. The product obtained had a purity of 85% and showed characteristic signals in the $^1$H-NMR-spectrum at δ=3.66 and 3.72 ppm for the two —COOMethyl groups of the two diastereomers.

EXAMPLE 4

Preparation of methyl (R,Z)-2-(2-pentenyl)-2-cyclopenten-1-yl malonate

A mixture of (Z)-2-(2-pentenyl)-2-cyclopenten-1-ol (17.8 g; 117 mmol), dimethyl malonate (17.8 g; 135 mmol), ground $KHCO_3$ (0.58 g; 5.8 mmol) and Novozym 435® (immobilized *Candida antarctica* from Novo Nordisk; 1.80 g) was gently swirled in a 100 ml flask connected to a Büchi rotavapor at 40° C. and 10 hPa. After 80 min., the reaction mixture was filtered, washed (sat. aq. $NaHCO_3$, sat. aq. NaCl), dried ($Na_2SO_4$) and concentrated (30.8 g). Bulb-to-bulb distillation afforded 15.5 g of volatiles (oven temp. 70° C./10–0.1 hPa) and ca. 11.14 g (95% pure, 36%, 97% ee) of the desired product which is isolated at an oven temperature of 80–130° C./0.06 hPa.

$^1$H-NMR: 0.96(t, J=7, 3H); 1.82(m, 1H); 2.04(quint., J=7, 2H); 2.20–2.50(m, 3H); 2.80(m, 2H); 3.38(s, 2H); 3.74(s, 3H); 5.35–5.52(m, 2H); 5.71(broad, 2H).

$^{13}$C-NMR: 167.1(s); 166.6(s); 140.8(s); 133.2(d); 131.0 (d); 125.1(d); 82.7(d); 52.4(q); 41.6(t); 30.8(t); 30.2(t); 26.1(t); 20.4(t); 14.2(q).

MS(m/e): 134(58), 119(92), 105(100), 91(64), 79(36), 77(28), 59(25), 41(32).

The starting (Z)-2-(2-pentenyl)-2-cyclopenten-1-ol was prepared as follows.

A solution of (Z)-2-(2-pentenyl)-2-cyclopenten-1-one (42.0 g, 280 mmol) in $Et_2O$ (50 ml) was added dropwise in 2 h to a mechanically stirred suspension of $LiAlH_4$ (5.32 g, 140 mmol) in $Et_2O$ (100 ml), thus maintaining a gentle reflux. After complete introduction, the mixture was heated for 15 min. at reflux (water bath), then cooled (icewater bath), hydrolyzed with 5% aq. NaOH (40 ml) and filtered. The concentrated filtrate (40.5 g) was distilled (in two portions) in a bulb-to-bulb apparatus (70° C. oven temp./0.1 hPa). Yield: 39.5 g (93%).

$^1$H-NMR(CDCl$_3$; 360 MHz): 0.96(t, J=7, 3H); 1.72(m, 1H); 1.92(broad, 1H, disappears in $D_2O$); 2.00–2.50(m, 5H); 2.88(m, 2H); 4.63(broad, 1H); 5.45(m, 2H); 5.54(broad s, 1H).

$^{13}$C-NMR(360 MHz): 144.9(s); 133.0(d); 127.6(d); 125.9 (d); 78.7(d); 33.9(t); 29.7(t); 26.1(t); 20.5(t); 14.3(q).

MS(m/e): 134($M^+$—$H_2O$, 20), 119(22), 105(22), 95(15), 91(28), 83(100), 81(15), 79(30), 77(18), 67(19), 55(25), 41(28), 39(24).

EXAMPLE 5
Preparation of (+)-methyl (R,Z)-2-(2-pentenyl)-2-cyclopentene-1-acetate The malonate obtained in Example 4 (9.90 g; ca. 95% pure, ca. 37.3 mmol) was added at 50° C. within 15 min. to a mechanically stirred suspension of washed NaH [55% in oil; 2.14 g (1.18 g pure NaH); 49 mmol] in THF (100 ml) (350 ml 3-neck flask, $N_2$). Immediate gas-evolution was observed, as well as the formation of a new precipitate. After heating the reaction mixture at reflux for 1 h, trimethylchlorosilane (8.50 g, 78.0 mmol) was added in 10 min. After refluxing the milky reaction mixture for 3 h, the product mixture was concentrated at reduced pressure, dissolved in ether, filtered through Celite®, concentrated and dried (13.81 g). The crude product was treated with N-methyl pyrrolidone (58.1 g), $H_2O$ (1.2 ml) and NaCl (2.90 g, 49 mmol) and heated at 140° C. for 30 min. The gas-evolution ($CO_2$) ceased after 15 min., indicating the end of the reaction. The cooled reaction mixture was poured into water, and the ester was extracted twice with ether, washed 3 times with $H_2O$, then with sat. aq. NaCl, dried ($Na_2SO_4$), filtered and concentrated. Bulb-to-bulb distillation of the residue (8.89 g) at 70–80° C. (oven temp.)/0.1 hPa afforded 7.05 g of the desired ester (92% pure, 80% yield, 97% ee).

The enantiomeric excess was determined on a column of the type Megadex 5 using a temperature program starting at 90° C. (constant for 6 min.), then heating to 180° C. at a rate of 2.5° C./min. and a hydrogen pressure of 16.9 psi. The desired enantiomer showed a retention time of 17.17 minutes (17.42 min. for the enantiomer).

$^1$H-NMR: 0.96(t, J=7, 3H); 1.58(m, 1H); 2.04(quint., J=7, 2H); 2.09–2.33(m, 4H); 2.57(dd, J=15 and 4, 1H); 2.62–2.83 (m, 2H); 2.96(m, 1H); 3.67(s, 3H); 5.35–5.50(m, 3H).

$^{13}$C-NMR: 173.7(s); 144.6(s); 132.8(d); 125.8(d); 125.3 (d); 51.5(q); 43.8(d); 38.4(t); 30.5(t); 30.4(t); 27.0(t); 20.5 (t); 14.2(q).

MS: 208($M^+$, 24), 177(14), 165(13), 152(34), 139(25), 134(41), 119(72), 105(92), 93(60), 91(28), 78(100), 77(53), 41(52).

EXAMPLE 6
Preparation of (+)-methyl (1R,2S,3R,Z)-2,3-epoxy-2-(2-pentenyl)-1-cyclopentane acetate 70% $H_2O_2$ (1.0 g, 20.6 mmol) was added to a solution of trifluoroacetic acid anhydride (6.28 g, 30.0 mmol) in $CH_2Cl_2$ (30 ml) at 0° C. The temperature was allowed to reach 20° C. (30 min.), then the solution was added dropwise to a suspension of the cyclopentene acetate prepared in Example 6 (2.80 g, 92% pure, 12.38 mmol) and $Na_2CO_3$ (4.30 g, 40.6 mmol) in $CH_2Cl_2$ (30 ml) at −50° C. After 90% addition (30 min.), the reaction was already complete. The reaction mixture was poured into aqueous $Na_2SO_3$ and extracted with ether. The organic phase was washed successively with $H_2O$, sat. aq. $NaHCO_3$ and sat. aq. NaCl, dried ($Na_2SO_4$), evaporated and distilled bulb-to-bulb (oven temp. 70–80° C./0.08 hPa), to obtain the desired product in a yield of 2.38 g (82%, 95% pure).

The enantiomeric excess was determined as described in Example 5, with the desired enantiomer having a retention time of 23.48 minutes (23.99 min. for its enantiomer).

$[\alpha]^{20}_D$=+2.12 (CHCl$_3$, c=0.03)

$^1$H-NMR: 0.96(t, J=7, 3H); 1.12(m, 1H); 1.61(m, 1H); 1.83(m, 1H); 1.95(m, 1H); 2.04(quint, J=7, 2H); 2.25–2.40 (3H); 2.52–2.70(m, 2H); 3.29(s, 1H); 3.68(s, 3H); 5.29(m, 1H); 5.49(m, 1H).

$^{13}$C-NMR: 173.5(s); 134.5(d); 122.6(d); 67.9(s); 62.4(d); 51.6(q); 37.8(d); 34.5(t); 27.2(t); 26.7(t); 26.6(t); 20.7(t); 14.1(q).

MS: 224($M^+$, 3), 206(6), 195(8), 177(18), 165(22), 155 (29), 151(30), 133(35), 121(30), 117(36), 107(43), 95(78), 93(74), 91(76), 79(76), 67(60), 55(70), 41(100).

EXAMPLE 7
Preparation of (+)-methyl (R,Z)-cis-3-oxo-2-(2-pentenyl)-1-cyclopentaneacetate A solution of the epoxide obtained in Example 6 (2.00 g, 95% pure, 8.48 mmol) in toluene (10 ml) was added at 3° C. in 10 min. to a stirred suspension of $AlCl_3$ (360 mg, 2.70 mmol) in toluene (20 ml). After an initiation time of 5–10 min., the yellow mixture turned red, and the reaction progressed rapidly. After 15 min., the mixture was poured into aq. sat. $NaHCO_3$ (30 ml) and stirred over night. The product was extracted with ether and the organic layer washed successively with $H_2O$ and sat. aq. NaCl, dried ($Na_2SO_4$) and evaporated. The concentrate (2.42 g) was purified by flash chromatography (silicagel F 60, 35–70 m; 15 g), using $CH_2Cl_2$ as eluant. There were obtained 1.36 g (68%, 95% pure) of the desired product, in an ee of 97%.

The enantiomeric excess was determined as described in Example 5, with the desired enantiomer showing a retention time of 25.43 minutes (25.82 min. for its enantiomer).

$[\alpha]^{20}_D$=+67.2 (CH$_3$Cl$_3$, c=0.06);+42.4 (MeOH, c=0.04)

$^1$H-NMR: 0.96(t, J=7, 3H); 1.83(m, 1H); 2.04(m, 2H); 2.08–2.42(m, 7H); 2.42(dd, J=16 and 5, 1H); 2.84(m, 1H); 3.69(s, 3H); 5.32(m, 1H); 5.44(m, 1H).

$^{13}$C-NMR: 218.8(s); 172.9(s); 133.5(d); 125.5(d); 52.7 (d); 51.7(q); 35.6(d); 35.3(t); 33.7(t); 25.7(t); 23.0(t); 20.7 (t); 14.1(q).

MS: 224($M^+$, 27), 206(7), 193(7), 177(10), 156(18), 151 (35), 133(17), 117(12), 109(25), 95(45), 83(100), 79(34), 77(18), 67(32), 55(33), 41(50).

The analytical data are identical with those reported by K. Weinges, U. Lernhardt, Liebigs Ann. Chem. 1990, 751.

EXAMPLE 8
Preparation of (+)-methyl (R)-2-pentyl-2-cyclopenten-1-yl malonate A suspension of racemic 2-(pentyl)-2-cyclopenten-1-ol (100 mg; 0.649 mmol), dimethylmalonate (100 mg; 0.757 mmol), ground $KHCO_3$ (7 mg; 0.05 mmol), diisopropyl ether (1.8 ml) and lipase (100 mg) was stirred in a 10 ml flask at room temperature (20–23° C.). Results are shown in the table below. The reaction was followed by GC method and the ee was determined by treating samples collected at the times indicated with N-methyl-N-trimethylsilyl-trifluoracetamide in dipropyl ether to silylate unreacted alcohol and effecting a chiral GC analysis (Megadex 5).

Results are shown in the table below

| Enzyme Activity Units/gr | Reaction time | % GC ester-ification | % ee of unreacted (−)-2-pentyl-2-cyclopentenol | Best theoretical % ee obtainable |
|---|---|---|---|---|
| Novozym ® 435 (Candida antarctica Fr B) 10,000 PLU | 20 hours | 37 | 61 | 59 |
| Chirazyme ® L-2, c.-f., C2 Iyo. (Candida antarctica Fr B) 5,000 U | 20 hours | 35 | 52 | 54 |
| Lipase QLM (Alcaligenes spp.) 60,000 U | 20 hours | 28 | 38 | 39 |
| Chirazyme ® L10 (Alcaligenes spp.) 20,000 U | 20 hours | 20 | 24 | 25 |
| Pseudomonas fluorescens 13,500 U | 8 days | 25 | 32 | 33 |
| Ps Amano ® (Pseudomonas cepacia) 30,000 U | 8 days | 27 | 34 | 37 |
| Candida rugosa or cylindracea 950,000 U | 8 days | 11 | 6 | 12.4 |
| Porcine pancreas lipase 42,000 U | 8 days | 8 | 5 | 8.7 |
| Lipozyme ® IM (Mucor miehei) 49 batch/U | 8 days | 18 | 19.5 | 22 |

As indicated by the table above, the progress of the reaction was determined by the ee of the unwanted substrate, (−)-2-(pentyl)-2-cyclopenten-1-ol.

EXAMPLE 9

(R)-Methyl-2-(2-pentynyl)-malonate

It was proceeded as described above for malonates of type VII [$R^1$=pentyl or (Z)-2-pentenyl].

Starting from 23.4 g of (±)-2-(2-pentynyl)-2-cyclopenten-1-ol (76% pure by GC), 14.7 g of distilled (R)-methyl-2-(2-pentynyl)-malonate (GC=90%) (b.p. 73–77°; 0.25 hPa) were isolated.

$^1$H-NMR: 1.14(t, J=7, 3H); 1.87(m, 1H); 2.15–2.55(5H); 2.93(AB, 2H); 3.37(s, 2H); 3.74(s, 3H); 5.72(m, 1H); 5.98 (broad s, 1H).

$^{13}$C-NMR: 167.1(s);166.6(s); 137.8(s); 132.6(d); 83.6(s); 82.1(d); 75.6(s); 52.5(q); 41.6(t); 31.0(t); 30.1(t); 18.6(t); 14.2(q); 12.4(t).

MS: 132(100), 117(98), 91(42), 77(17), 59(2), 41(23).

The starting 2-(2-pentynyl)-2-cyclopenten-1-ol was prepared as follows. 29,9 g of 89% pure 2-(2-pentynyl)-2-cyclopenten-1-one were added at 0° to a stirred suspension of LiAlH$_4$ (2.50 g) in Et$_2$O (300 ml). After 2 h, the mixture was carefully treated with water (2.5 ml), 5% aqu. NaOH (2.5 ml) and more water (7.5 ml). After 10 min, the suspension was dried (Na$_2$SO$_4$), filtered on Celite and the filtrate evaporated and distilled (72°/0.5 hPa). Yield: 23.4 g (76% pure).

$^1$H-NMR: 1.14(t, J=7, 3H); 1.75(m, 1H); 1.86(s, OH); 2.15–2.50(5H); 3.04(AB, 2H) 4.72 (broad, 1 H); 5.28(broad s, 1H).

$^{13}$C-NMR: 141.6(s); 129.3(d); 83.5(s); 76.3(s); 34.0(t); 29.6(t); 18.5(t); 14.2(g); 12.4(t).

MS: 149(1), 91(16), 83(100), 79(14), 77(14), 55(15).

EXAMPLE 10

(R)-Methyl-2-(2-pentynyl)-2-cyclopentene-1-acetate

It was proceeded as described above for esters III [R=Me, $R^1$=pentyl or (Z)-2-pentenyl].

Starting from 14.7 g of (R)-methyl-2-(2-pentynyl)-malonate (90% pure by GC), 9.40 g of (R)-Methyl-2-(2-pentynyl)-2-cyclopentene-1-acetate (90% pure by GC) were obtained after distillation (bulb-to-bulb; oven temp. 100°; 0.15 hPa). The ee was determined by chiral GC (Megadex 5, as usual): 96% ee.

$^1$H-NMR: 1.13(t, J=7, 3H); 1.61(m, 1H); 2.12–2.38(6H); 2.60(m, 1H); 2.90(AB, 2H) 3.02(m, 1H); 3.67(s, 3H); 5.66 (split s, 1H).

$^{13}$C-NMR: 173.5(s); 141.3(s); 127.1(d); 83.4(s); 76.1(s); 51.5(q); 43.2(d); 38.2(t); 30.7(t); 30.4(t); 19.4(t); 14.2(q); 12.4(t).

MS: 206(M$^+$, 13), 177(13), 146(17), 133(40), 132(40), 131(40), 117(100), 105(45), 91(67), 79(43).

EXAMPLE 11

Methyl-(1R,2S,3R)-2,3-epoxy-2-(2-pentynyl)-1-cyclopentene acetate

It was proceeded as described above in Example 6 [R=Me, $R^1$=(Z)-2-pentenyl]. Starting from 1.00 g of (R)-methyl-2-(2-pentynyl)-2-cyclopentene-1-acetate (90% pure by GC), 0.83 g of methyl-(1R,2S,3R)-2,3-epoxy-2-(2-pentynyl)-1-cyclopentene acetate (90% pure by GC) were obtained after distillation (bulb-to-bulb; oven temp. 130°; 0.25 hPa).

$^1$H-NMR: 1.12(t, J=7, 3H); 1.10-1.20(m, 1H); 1.66(m, 1H); 1.85(m, 1H); 1.96(m, 1H); 2.15(m, 2H); 2.30(m, 1H); 2.46–2.56(m, 2H); 2.64–2.67(m, 2H); 3.43(s, 1H); 3.69(s, 3H).

$^{13}$C-NMR: 173.3(s); 84.0(s); 73.7(s); 66.6(s); 63.4(d); 51.6(q); 37.3(d); 34.3(t); 26.9(t); 26.4(t); 20.7(t); 14.0(q); 12.4(t).

MS: 222(M$^+$, 2), 207(7), 193(14), 163(19), 153(28), 147 (52), 133(37), 122(58), 107(47), 105(47), 91(78), 79(61), 55(62), 41(100).

EXAMPLE 12

(+)-Methyl-(1R,2S,3R,Z)-2,3-epoxy-2-(2-pentenyl)-1-cyclopentane acetate [≡I. R=Me, $R^1$=(Z)-2-pentenyl]

222 mg of methyl-(1R,2S,3R)-2,3-epoxy-2-(2-pentynyl)-1-cyclopentene acetate (97% pure by GC) were dissolved in cyclohexane (5 ml) and hydrogenated with Lindlar catalyst (11.1 mg). After 80 min, GC-control showed full conversion. The reaction mixture was filtered over Celite. Evaporation of the solvent and distillation (bulb-to-bulb; oven temp. 130°; 0.20 hPa) afforded 220 mg of 91% pure (+)-methyl-(1R,2S,3R,Z)-2,3-epoxy-2-(2-pentenyl)-1-cyclopentane acetate which was in all respects identical with the reference compound (+)-methyl-(1R,2S,3R,Z)-2,3-epoxy-2-(2-pentenyl)-1-cyclopentane acetate.

What is claimed is:

1. A compound of formula

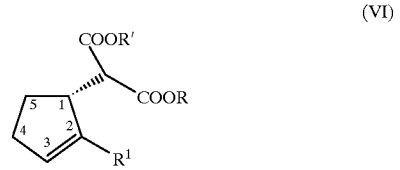

(VI)

having a cyclanic (1R) configuration, in which R is an alkyl group from $C_1$ to $C_4$, linear or branched, R' is hydrogen or a triorganylsilyl group, and $R^1$ is an alkyl, alkenyl or alkynyl group from $C_4$ to $C_6$, linear or branched.

2. A compound according to claim 1, wherein R is a methyl group and $R^1$ is a n-pentyl or a (Z)-2-pentenyl group.

3. A process for the preparation of an ester of formula

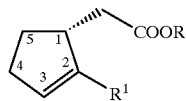

(III)

starting from a compound of formula

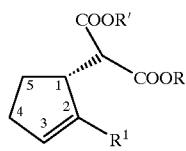

(VI)

which formulae (VI) and (III) have a cyclanic (1R) configuration and in which R, R' and $R^1$ have the meaning indicated in claim 1, wherein said compound (VI) undergoes a decarboxylation reaction under conditions susceptible of providing compound (III).

4. A process for the preparation of a malonate of formula (VI) as defined in claim 1, comprising the Claisen rearrangement of a compound of formula

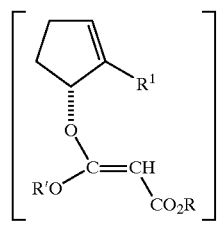

(VIII)

having a cyclanic (1R)-configuration and in which R, R' and $R^1$ have the meaning defined in claim 1, under conditions susceptible of providing said compound of formula (VI).

5. The process according to claim 4, which further comprises the conversion of a cyclopentenone of formula

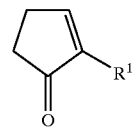

(V)

into a malonic ester of formula

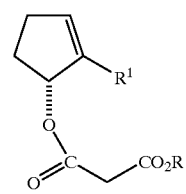

(VII)

having a cyclanic (1R)-configuration and in which R and $R^1$ have the meaning defined in claim 1, followed by the enolization, or the enolization plus silylation, of the thus-obtained compound to form a compound of formula (VIII) as defined in claim 4.

6. The process according to claim 5, wherein said silylation is carried out using trimethylsilylchloride.

7. The process according to claim 4, wherein, in the formulae R is a methyl group and $R^1$ a n-pentyl or a (Z)-2-pentenyl group.

* * * * *

UNITED STATES PATENT AND TRADEMARK OFFICE
CERTIFICATE OF CORRECTION

PATENT NO. : 6,262,288 B1
DATED : July 17, 2001
INVENTOR(S) : Fehr et al.

It is certified that error appears in the above-identified patent and that said Letters Patent is hereby corrected as shown below:

<u>Title page,</u>
Item [56] References Cited,
Under the heading "U.S. PATENT DOCUMENTS" and between the second and third listed references, please insert the following reference,
-- 5,874,600  2/1999  Rautenstrauch et al. --

Under the heading "FOREIGN DOCUMENTS" and after the one listed reference, please correct the following references,
-- 9533735  12/1995  (WO) --
-- 9852687  11/1998  (WO) --

Under the heading "OTHER PUBLICATIONS", please insert the following references,
-- E.J. Corey et al., "A Stable and Easily Prepared Catalyst for the Enantioselective Reduction if Ketones. Applications to Multistep Syntheses", *J. Am. Chem. Soc.*, Vol. 109, pp. 7925-7926 (1987). --
-- S. Itsuno et al., "Catalytic Behavior of Optically Active Amino Alcohol-Borane Complex in the Enantioselective Reduction of Acetophenone Oxime O-Alkyl Ethers", *Bull- Chem. Soc. Jpn.*, Vol. 60, pp. 395-396 (1987). --

-- T. Kitahara et al., "A simple and Efficient Synthesis of (±)-Methyl Dihydroepijasmonate", *Agric. Biol. Chem.*, Vol. 50, No. 7, pp. 1867-1872 (1986). --

-- T. Kitahara et al., "Synthesis of (±)-Methyl Epijasmonate and (±)-Methyl Cucurbate", Agric. Biol. Chem., Vol. 51, No. 4, pp. 1129-1133 (1987) --.

UNITED STATES PATENT AND TRADEMARK OFFICE
CERTIFICATE OF CORRECTION

PATENT NO. : 6,262,288 B1
DATED : July 17, 2001
INVENTOR(S) : Fehr et al.

It is certified that error appears in the above-identified patent and that said Letters Patent is hereby corrected as shown below:

-- D. Mathre et al., "A Practical Enantioselective Sytheses of $N$, $N$-Diaryl-2-pyrrolidinemethanol. Preparation and Chemistry of the Corresponding Oxazabirilidines", J. Org. Chem., Vol. 56, pp. 751-726 (1991). --
-- V. Singh, "Practical and Useful Methods for the Enantioselective Reduction of Unsymmetircal Ketones", Synthesis, pp. 605-617 (1992). --

Signed and Sealed this

Fourteenth Day of May, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,262,288 B1
DATED : July 17, 2001
INVENTOR(S) : Fehr et al.

It is certified that error appears in the above-identified patent and that said Letters Patent is hereby corrected as shown below:

<u>Title page,</u>
Item [56] References Cited,
Under the heading "U.S. PATENT DOCUMENTS" and between the second and third listed references, please insert the following reference,
    -- 5,874,600  2/1999  Rautenstrauch et al. --

Under the heading "FOREIGN DOCUMENTS" and after the one listed reference, please correct the following references,
    -- 9533735  12/1995  (WO) --
    -- 9852687  11/1998  (WO) --

Under the heading "OTHER PUBLICATIONS", please insert the following references,
-- E.J. Corey et al., "A Stable and Easily Prepared Catalyst for the Enantioselective Reduction of Ketones. Applications to Multistep Syntheses", *J. Am. Chem. Soc.*, Vol. 109, pp. 7925-7926 (1987). --
-- S. Itsuno et al., "Catalytic Behavior of Optically Active Amino Alcohol-Borane Complex in the Enantioselective Reduction of Acetophenone Oxime *O*-Alkyl Ethers", Bull. Chem. *Soc. Jpn.*, Vol. 60, pp. 395-396 (1987). --

-- T. Kitahara et al., "A Simple and Efficient Synthesis of (±)-Methyl Dihydroepijasmonate", *Agric. Biol. Chem.*, Vol. 50, No. 7, pp. 1867-1872 (1986). --

-- T. Kitahara et al., "Synthesis of (±)-Methyl Epijasmonate and (±)-Methyl Cucurbate", *Agric. Biol. Chem.*, Vol. 51, No. 4, pp. 1129-1133 (1987) --.

UNITED STATES PATENT AND TRADEMARK OFFICE
CERTIFICATE OF CORRECTION

PATENT NO.   : 6,262,288 B1
DATED        : July 17, 2001
INVENTOR(S)  : Fehr et al.

It is certified that error appears in the above-identified patent and that said Letters Patent is hereby corrected as shown below:

-- D. Mathre et al., "A Practical Enantioselective Sytheses of α, α-Diaryl-2-pyrrolidinemethanol. Preparation and Chemistry of the Corresponding Oxazaborolidines", *J. Org. Chem.*, Vol. 56, pp. 751-726 (1991). --
-- V. Singh, "Practical and Useful Methods for the Enantioselective Reduction of Unsymmetircal Ketones", *Synthesis*, pp. 605-617 (1992). --

This certificate supersedes Certificate of Correction issued May 14, 2002

Signed and Sealed this

Twenty-fourth Day of September, 2002

*Attest:*

*Attesting Officer*

JAMES E. ROGAN
*Director of the United States Patent and Trademark Office*